United States Patent [19]

Shutske et al.

[11] Patent Number: 5,210,087
[45] Date of Patent: May 11, 1993

[54] 9-AMINOTETRAHYDROACRIDINES AND RELATED COMPOUNDS

[75] Inventors: Gregory M. Shutske, Flemington; Kevin J. Kapples, Little York, both of N.J.; John D. Tomer, Perkasie, Pa.

[73] Assignee: Hoechst-Roussel Pharmaceuticals Inc., Somerville, N.J.

[21] Appl. No.: 654,691

[22] Filed: Feb. 13, 1991

[51] Int. Cl.$^5$ .................. C07D 219/10; A61K 31/44
[52] U.S. Cl. .................................. 514/297; 546/103; 546/14; 546/79; 548/241
[58] Field of Search .................. 546/103; 514/297

[56] References Cited

U.S. PATENT DOCUMENTS

| | | | |
|---|---|---|---|
| 3,232,945 | 2/1966 | Sigal et al. | 546/93 |
| 4,631,286 | 12/1986 | Shutske et al. | 514/297 |
| 4,695,573 | 9/1987 | Shutske et al. | 514/290 |

FOREIGN PATENT DOCUMENTS 0179383  4/1986  European Pat. Off. .
8902739  4/1989  PCT Int'l Appl. ............... 514/291
8902740  4/1989  PCT Int'l Appl. ............... 546/93

OTHER PUBLICATIONS

G. M. Shutske, et al., Journal of Medicinal Chemistry, vol. 32, pp. 1805 to 1813 (Aug., 1989), entitled "9-Amino-1,2,3,4-tetrahydroacridin-1-ols: Synthesis and Evaluation as Potential Alzheimer's Disease Therapeutics".

A. A. Akhrem, et al., Synthesis, p. 43 (Jan., 1978), entitled "A Convenient One-Step Synthesis of Tetrahydrobenzisoxazoles via 1,3-Cycloaddition of Nitrile Oxides to Cyclohexane-1,3-dione Derivatives".

Primary Examiner—Alan L. Rotman
Attorney, Agent, or Firm—Raymond R. Wittekind

[57] ABSTRACT

Novel 9-aminotetrahydroacridines and related compounds, intermediates and processes for the preparation thereof, and a method of relieving memory dysfunction are disclosed.

7 Claims, No Drawings

9-AMINOTETRAHYDROACRIDINES AND RELATED COMPOUNDS

The present invention relates to 9-aminotetrahydroacridines and related compounds. More particularly, the present invention relates to 9-amino-1,2,3,4-tetrahydroacridines and related compounds of formula 1

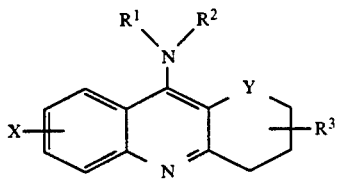

wherein Y is C=O or CHOH; $R^1$ is hydrogen or loweralkyl; $R^2$ is hydrogen, loweralkyl, or phenylloweralkyl; $R^3$ is hydrogen, $OR^4$ wherein $R^4$ is hydrogen, $COR^5$ wherein $R^5$ is loweralkyl; X is hydrogen, loweralkyl, halogen, loweralkoxy, hydroxy, or trifluoromethyl, the geometric or optical isomers thereof, the N-oxides thereof, or the pharmaceutically acceptable acid addition salts thereof, which are useful in relieving memory dysfunction and are thus indicated in the treatment of Alzheimer's disease.

Preferred 9-amino-1,2,3,4-tetrahydroacridines and related compounds of the present invention are those wherein Y is C=O or CHOH and $R^3$ is $OR^4$ wherein $R^4$ is hydrogen.

The present invention also relates to 9-aminosilyl-dihydroacridinones of formula 2

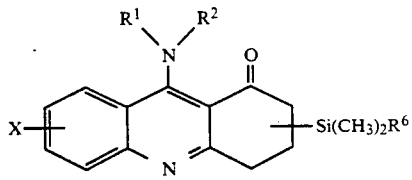

wherein $R^1$ is hydrogen or loweralkyl, $R^2$ is hydrogen, loweralkyl, or phenylloweralkyl, $R^6$ is phenyl or fluoro; and X is hydrogen, loweralkyl, halogen, loweralkoxy, hydroxy, or trifluoromethyl and dihydrobenzisoxazolines of formula 3

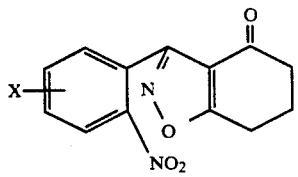

wherein X is hydrogen, loweralkyl, halogen, loweralkoxy, hydroxy, or trifluoromethyl, which are useful as intermediates for the preparation of the 9-aminoetrahydroacridindiols and related compounds of the present invention.

As used throughout the specification and appended claims, the term "alkyl" refers to a straight or branched chain hydrocarbon radical containing no unsaturation and having 1 to 8 carbon atoms. Examples of alkyl groups are methyl, ethyl, 1-propyl, 2-propyl, 1-butyl, 1-pentyl, 3-hexyl, 4-heptyl, 2-octyl and the like. The term "alkoxy" refers to a monovalent substituent which consists of alkyl group linked through an ether oxygen having its free valence bond from the ether oxygen. Examples of alkoxy groups are methoxy, ethoxy, propoxy, 1-butoxy, 1-pentoxy, 3-hexoxy, 4-heptoxy, 2-octoxy and the like. The term "alkanol" refers to a compound formed by a combination of an alkyl group and hydroxy radical. Examples of alkanols are methanol, ethanol, 1- and 2-propanol, 2,2-dimethylethanol, hexanol, octanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid and the like. The term "halogen" refers to a member of the family fluorine, chlorine, bromine, or iodine. The term "alkanoyl" refers to the radical formed by removal of the hydroxy function from an alkanoic acid. Examples of alkanoyl groups are formyl, acetyl, propionyl, 2,2-dimethylacetyl, hexanoyl, octanoyl, decanoyl and the like. The term "alkanoic acid anhydride" refers to a compound formed by combination of two alkanoyl radicals and one oxy radical. Examples of alkonoic acid anhydrides are acetic acid anhydride, propanoic acid anhydride, 2,2-dimethylacetic acid anhydride, hexanoic acid anhydride, octanoic acid anhydride and the like. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by synthesis from optically active precursors.

In the formulas of the 9-aminotetrahydroacridindiols presented herein the hydroxyl groups attached to the cyclohexane ring system may be either in the cis or trans configuration, i.e., the hydroxyl groups may be, respectively, on the same side or on opposite sides of the average plane of the cyclohexane ring. Unless otherwise specified, each formula contemplates both the cis and trans isomers. In the structural formula used herein, heavy lines (———) indicate that the substituent is above the average plane of the cyclohexane ring and broken lines (- - - -) indicate that the substituent is below the average plane of ring. A wavy line (∼∼∼) indicates the substituent may be above or below the average plane of the ring.

The present invention comprehends all optical isomers and racemic forms thereof of the compounds disclosed and claimed herein and the formulas of the compounds shown herein are intended to encompass all possible optical isomers of the compounds so depicted.

The novel 9-aminotetrahydroacridindiols of the present convention are prepared by the processes delineated in Reaction Schemes A and B.

To prepare a 9-amino-1,2,3,4-tetrahydroacridin-1,4-diol 9 of the present invention, a 2-nitrobenzhydroxamic chloride 4 is condensed with a cyclohexan-1,3-dione enamine 5 to provide a 6,7-dihydro-3-(2-nitrophenyl)benzisoxazol-4(5H)-one 6 which is reductively cyclized to a 9-amino-3,4-dihydroacridin-1(2H)-one N-oxide 7, rearranged to a 4-alkanoyloxy-9-amino-3,4- dihydroacridin-1(2H)-one 8, and reduced and cleaved to a diol 9. See Reaction Scheme A.

The condensation of a hydroxamic acid chloride 4 with an enamine 5 (e.g., an enamine where $R^8$ and $R^9$ are alkyl, or together form a heterocycle such as morpholine) to a benzisoxazole 6 is performed in an ethereal solvent such as 1,2-dimethoxylethane, 2-methoxyethyl ether, dioxane, and tetrahydrofuran, tetrahydrofuran being preferred. While the condensation temperature is not narrowly critical, it is preferred to perform the reaction at the reflux temperature of the reaction medium.

The reductive cyclization of a benzisoxazolone 6 to an aminoacridinone N-oxide 7 is conducted by hydrogenating benzisoxazole 6 in the presence of a catalyst under acidic conditions in an ethereal solvent. Among catalysts, there may be mentioned platinum, palladium, rhodium and ruthenium, unsupported or supported on, for example, carbon, alumina, or calcium carbonate. Palladium-on-carbon is preferred. Included among ethereal solvents are 1,2-dimethoxyethane, 2-methoxyethyl ether, dioxane, and tetrahydrofuran. Tetrahydrofuran is preferred. Acidic reaction conditions are obtained by conducting the reaction in dilute mineral acid, i.e. dilute hydrochloric, hydrobromic, nitric, or phosphoric acid. 5% Hydrochloric acid is preferred. Under these conditions, the hydrogenation proceeds at a reasonable rate under a hydrogen pressure within the range of about atmospheric pressure to about 100 psi. A hydrogenation pressure of about 50 psi is preferred.

The rearrangement of an acridinone N-oxide 7 to a 4-alkanoyloxyacridinone 8 is effected by means of an alkanoic acid anhydride of formula 16

$$(R^5CO)_2O \qquad 16$$

wherein $R^5$ is alkyl, the anhydride 16 acting as a reactant and the reaction solvent. The preferred anhydride is acetic anhydride. The rearrangement proceeds readily at the reflux temperature of the medium; reduced rearrangement temperatures to as low as ambient temperature may be employed, however.

The reduction and cleavage are carried out by treating a 4-alkanoyloxy-9-aminoacridinone 8 with an alkali metal aluminum hydride, for example, lithium, sodium, or potassium aluminum hydride, in an ethereal solvent, for example, diethyl ether, 1,2-dimethoxyethane, 2-methoxyethyl ether, dioxane, or tetrahydrofuran. Lithium aluminum hydride and tetrahydrofuran are the preferred alkali metal hydride and ethereal solvent, respectively. The temperature at which the reduction and cleavage are preformed is not critical; however, it is preferred to perform the reaction at about ambient temperature. Under the aforedescribed conditions, a mixture of the cis- and trans-acridindiols 9a and 9b, respectively is formed, which is separated by flash chromatography.

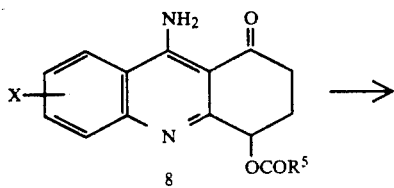

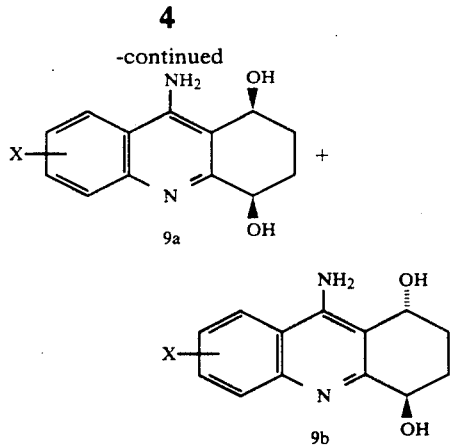

To gain entry into the 9-amino-1,2,3,4-tetrahydroacridin-1,3-diol series, i.e., to prepare diols of formula 15, an anthranilonitrile 10 is condensed with a 5-(phenyldialkylsilyl)-1,3-cyclohexanedione 11 to afford a 3-(oxocyclohex-1-enyl)-2-aminobenzonitrile 12, which is cyclized to a 9-amino-3-(phenyldialkylsilyl)acridinone 13 and, in turn, converted to a 9-amino-3-hydroxyacridinone 14 and reduced to a diol 15.

The condensation of an aniline 10 with a dione 11 to enaminone 12 is conveniently conducted in the presence of an acid catalyst in an aromatic solvent at the boiling point of the reaction medium with water collection in a Dean-Stark apparatus. Acid catalysts include mineral acids (e.g., sulfuric acid) and organic sulfonic acids (e.g., methanesulfonic acid, benzenesulfonic acid, and para-toluenesulfonic acid). Aromatic solvents include benzene, toluene, xylene, and mesitylene. The preferred condensation medium consists of para-toluenesulfonic acid and toluene.

The cyclization of an enaminone 16 to a 9-aminoacridinone 13 is achieved in an ethereal solvent (e.g., 1,2-dimethoxyethane, 2-methoxyethyl ether, dioxane, or tetrahydrofuran) containing a base (e.g., an alkali metal carbonate such as lithium, sodium, or potassium carbonate) and a promoter (e.g., a cuprous halide such a cuprous bromide or chloride). Preferred among the ethereal solvents, bases, and promoters are tetrahydrofuran, potassium carbonate, and cuprous chloride, respectively. While the cyclization proceeds at a reasonable rate at about ambient temperature, to expedite the transformation, elevated reaction temperatures to the reflux temperature of the medium may be employed. The preferred cyclization temperate is the reflux temperature of the reaction medium.

The conversion of a 3-(phenyldialkylsilyl)acridinone 13 to a 3-hydroxyacridinone 14 is effected by fluorination of 13 wherein $R^{11}$ is phenyl to a 3-(fluorodialkylsilyl)acridinone 13 wherein $R^{11}$ is fluoro followed by oxidative cleavage of the silyl group. The fluorination is accomplished in a halocarbon (e.g., dichloromethane, trichloromethane, or 1,1- or 1,2-dichloroethane) in the presence of tetrafluoroboric acid or its etherate at about ambient temperature.

The oxidative cleavage is accomplished by means of hydrogen peroxide in an ether/alkanol solvent in the presence of an alkali fluoride (e.g., lithium, sodium, or potassium fluoride) and an alkali bicarbonate (e.g., lithium, sodium, or potassium bicarbonate) at a reaction temperature of about 0° to about 25° C. Among ethereal components of the solvent, there may be mentioned 1,2-dimethoxymethane, 2-methoxy ethyl ether, dioxane, tetrahydrofuran, and mixtures thereof. Among alkanol components, there may be mentioned methanol, ethanol and 1-, or 2-propanol. Tetrahydrofuran/methanol is the preferred solvent. Potassium fluoride and sodium bicarbonate are the preferred alkali fluoride and alkali bicarbonate, respectively. It is also preferable to perform the oxidative cleavage initially at about 0° C. and finally at about 25° C.

The reduction of a 9-amino-3-hydroxyacridin-1(2H)-one 14 to a 9-aminoacridindiol 15 is conducted in an ethereal solvent (e.g., diethyl ether, 1,2-dimethoxyethane, 2-methoxyethyl ether, dioxane, or tetrahydrofuran) by means of an alkali metal trialkylborohydride of formula 17 (e.g., lithium, sodium, or potassium trimethyl, triethyl, tri-1- or 2-propylborohydride) at about ambient temperature. Lithium triethylborohydride in tetrahydrofuran is the preferred reduction medium. Under the aforedescribed conditions, a mixture of the cis- and trans-acridindiols 15a and 15b, respectively is formed, which is separated by flash chromatography.

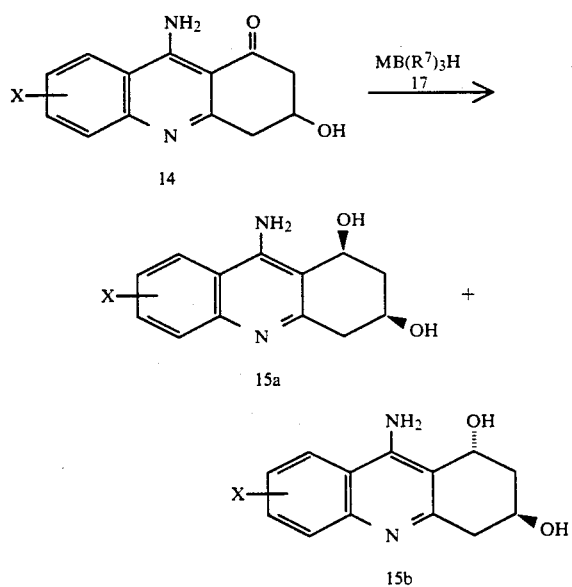

A 9-aminoacridin-1,2-diol 18 may be prepared from a 2-aminobenzonitrile 10 and a 6-(phenyldialkylsilyl)-1,3-cyclohexandione 19 by following the processes shown in Reaction Scheme B.

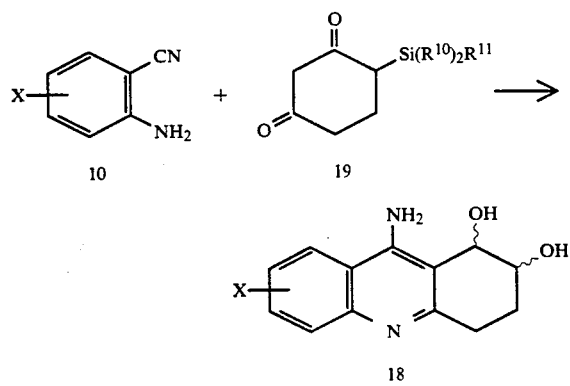

Alkylation of the amino group of the 9-aminoacridindiols and derivatives thereof, 9-aminohydroxyacridinones and 9-aminosilylacridinones of the present invention, i.e., compounds of the formulas 8,9,13,14, and 15 to provide 9-alkylamino- and 9-dialkylaminoacridindiols, -1-hydroxyacridinones, and -silylacridinones, may be preformed by utilizing conventional processes.

The 9-aminotetrahydroacridines of the present invention are useful as agents for the relief of memory dysfunction, particularly dysfunctions associated with decreased cholinergic activity such as those found in Alzheimer's disease. Relief of memory dysfunction activity of the instant compounds is demonstrated in the dark avoidance assay, an assay for the determination of the reversal of the effects of scopolamine induced memory deficits associated with decreased levels of acetylcholine in the brain. In this assay, three groups of 15 male CFW mice were used—a vehicle/vehicle control group, a scopolamine/vehicle group, and a scopolamine/drug group. Thirty minutes prior to training, the vehicle/vehicle control group received normal saline subcutaneously, and the scopolamine/vehicle and scopolamine/drug groups received scopolamine subcutaneously (3.0 mg/kg, administered as scopolamine hydrobromide). Five minutes prior to training, the vehicle/vehicle control and scopolamine/vehicle groups received distilled water and the scopolamine/drug group received the test compound in distilled water.

The training/testing apparatus consisted of a plexiglass box approximately 48 cm long, 30 cm high and tapering from 26 cm wide at the top to 3 cm wide at the bottom. The interior of the box is divided equally by a vertical barrier into a light compartment (illuminated by a 25-watt reflector lamp suspended 30 cm from the floor) and a dark compartment (covered). A hole (2.5 cm wide and 6 cm high) at the bottom of the barrier and a trap door that can be dropped to prevent an animal from passing between the two compartments is present. A Coulbourn Instruments small animal shocker was attached to two metal plates that ran the entire length of the apparatus, and a photocell was placed in the dark compartment 7.5 cm from the vertical barrier and 2 cm above the floor. The behavioral session was controlled by a PDP 11/34 minicomputer.

At the end of the pretreatment interval, an animal was placed in the light chamber directly under the light fixture, facing away from the door to the dark chamber. The apparatus was then covered and the system activated. If the mouse passed through the barrier to the dark compartment and broke the photocell beam within 180 seconds, the trap door dropped to block escape to the light compartment and an electric shock was administered at an intensity of 0.4 milliamps for three seconds. The animal was then immediately removed from the dark compartment and placed in its home cage. If the animal failed to break the photocell beam within 180 seconds, it was discarded. The latency is seconds for each mouse was recorded.

Twenty-four hours later, the animals were again tested in the same apparatus except that no injections were made and the mice did not receive a shock. The test day latency in seconds for each animal was recorded and the animals were then discarded.

The high degree of variability (due to season of the year, housing conditions, and handling) found in one trial passive avoidance paradigm is well known. To control for this fact, individual cutoff (CO) values were determined for each test, compensating for interest variability. Additionally, it was found that 5 to 7% of the mice in the scopolamine/vehicle control groups were insensitive to scopolamine at 3 mg/kg, sc. Thus, the CO value was defined as the second highest latency time in the control group to more accurately reflect the 1/15 expected control responders in each test group. Experiments with a variety of standards repeated under a number of environmental conditions led to the development of the following empirical criteria: for a valid test, the CO value had to be less than 120 sec and the vehicle/vehicle control group had to have at least 5/15 animals with latencies greater than CO. For a compound to be considered active the scopolamine/compound group had to have at least 3/15 mice with latencies greater than CO.

The results of the dark avoidance test are expressed as the number of animals per group (%) in which this scopolamine induced memory deficit is blocked as measured by an increase in the latency period. Relief of memory dysfunction activity for representative compounds of the present invention is presented in the Table 1.

TABLE 1

| Compound | Dose (mg/kg, sc) | Percent of Animals with Scopolamine Induced Memory Deficit Reversal |
|---|---|---|
| 9-amino-1,2,3,4-tetrahydro-1,3-acridinediol maleate, mp 158–160° C. | 3.0 | 27 |
| 9-amino-1,2,3,4-tetrahydro-1,3-acridinediol maleate, mp 179–180° C. | 3.0 | 20 |
| 9-amino-1,2,3,4-tetrahydro-1,4-acridinediol, mp 200° C. (dec) | 3.0 | 21 |
| physostigmine | 0.31 | 20 |

Scopolamine induced memory deficit reversal is achieved when the present 9-aminotetrahydroacridines are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The 9-aminotetrahydroacridines of the present invention exhibit low toxicity (lethality) as determined in the primary overt effects assay. In this assay, groups of four male Wistar rats (125–300 g) are used. Prior to testing, the animals are housed for at least 24 hrs in a climate controlled room with food and water available ad libitum. On the day of testing, the animals are removed from their home cages and placed 4/box in white translucent plastic boxes (45×25×29 cm) with metal bar covers and transported to the test room. Food and water are not available at any time during the day of testing.

Compounds are prepared using distilled water and, if insoluble, a surfactant is added and the resulting suspension is kept constantly agitated.

Prior to drug administration, all animals are examined for any overt abnormalitities which may subsequently be confused as a drug effect. These include eye position, eye clarity, blood around eyes or nose, unusual gait, abnormal behavior during handling and abnormal behavior in the plastic boxes. Core temperatures are then determined (either rectally or intraperitoneally).

Animals are then administered drug intraperitoneally with the control group receiving vehicle.

Animals are observed in the plastic boxes continuously for one hour after drug administration and any overt effects are noted. A complete examination is made on each animal at 1,2,4 and 6 hrs postdrug and the results are recorded. The room should be quiet during testing. Obvious effects seen between these times are recorded. The animals are given food and water after 6 hours and kept for 24 hrs, when their general condition is observed. Time of death is noted for each animal and the time at which the first and last deaths occur are reported.

The results are expressed as the number of deaths per group. Toxicity of representative compounds of the present invention is presented in Table 2.

TABLE 2

| Compound | Dose (mg/kg, sc) | Number of Deaths per Group |
|---|---|---|
| 9-amino-1,2,3,4-tetrahydro-1,3-acridinediol maleate, mp 158–160° C. | 80 | 0 |
| 9-amino-1,2,3,4-tetrahydro-1,3-acridinediol maleate, mp 179–180° C. | 80 | 0 |
| 9-amino-1,2,3,4-tetrahydro-1,4-acridinediol, mp 200° C. (dec) | 80 | 0 |

Compounds of the invention include:
a. 9-methylamino-1,2,3,4-tetrahydro-1,4-acridinediol;
b. 9-(2-phenylethylamino)-1,2,3,4-tetrahydro-1,4-acridinediol;
c. 9-amino-8-methyl-1,2,3,4-tetrahydro-1,4-acridinediol;
d. 9-amino-7-fluoro-1,2,3,4-tetrahydro-1,4-acridinediol;
e. 9-amino-6-methoxy-1,2,3,4-tetrahydro-1,4-acridinediol;
f. 9-amino-6-hydroxy-1,2,3,4-tetrahydro-1,4-acridinediol;
g. 9-amino-5-trifluoromethyl-1,2,3,4-tetrahydro-1,4-acridinediol;
h. 9-amino-7-fluoro-3,4-dihydroacridin-1(2H)-one;
i. 9-amino-6-methoxy-3,4-dihydroacridin-1(2H)-one;
j. 9-amino-6-hydroxy-3,4-dihydroacridin-1(2H)-one; and
k. 9-amino-5-trifluoromethyl-3,4-dihydroacridin-1(2H)-one.

Effective amounts of the compounds of the invention may be administered to a subject by any one of various methods, for example, orally as in capsules or tablets, parenterally in the form of sterile solutions or suspensions, and in some cases intravenously in the form of sterile solutions. The basic final products and intermediates, while effective themselves, may be formulated and administered in the form of their pharmaceutically acceptable acid addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0-300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

6,7-Dihydro-3-(2-nitrophenyl)-1,2-benzisoxazol-4(5H)-one

To a solution of 1,3-cyclohexadione morpholine enamine (20.8 g), tetrahydrofuran (150 ml), and triethylamine (2 ml) at reflux was added a solution of 2-nitrobenzhydroxamic chloride (17.7 g) in tetrahydrofuran (100 ml) dropwise over 2 hrs. The reaction mixture was heated under reflux for 1 hr and then evaporated. The residue was partitioned between 3N hydrochloric acid and ethyl acetate. The ethyl acetate layer was washed with 3N hydrochloric acid, 10% sodium carbonate solution, saturated sodium chloride solution, dried over anhydrous magnesium sulfate, filtered, and the filtrate was evaporated. The reside was chromatographed on silica gel with ethyl acetate as the eluent. The appropriate fractions were collected and evaporated. The residue was recrystallized from dichloromethane/hexanes to yield 15.0 g (66%) of product, mp 125°-127° C.

Analysis: Calculated for $C_{13}H_{10}N_2O_4$: 60.47% C; 3.90% H; 10.85% N. Found: 60.81% C; 4.13% H; 10.88% N.

EXAMPLE 2

9-Amino-3,4-dihydroacridin-1(2H)-one N-oxide

A mixture of 6,7-dihydro-3-(2-nitrophenyl)-1,2-benzisoxazole-4(5H)-one, (7.0 g), 5% palladium-on-carbon (0.7 g), 5% hydrochloric acid (11 ml), and tetrahydrofuran (200 ml) was hydrogenated at 50 psi. After one hr, methanol (1 l) was added, and the mixture was filtered through celite. The filtrate was concentrated, and the concentrate was flash chromatographed (silica, 3-20% methanol/ethyl acetate; 40% methanol/dichloromethane). The appropriate fractions were collected and concentrated. The residue was triturated with methanol/diethyl ether to yield 5.4 g (83%) of product, mp 290° C. (dec).

EXAMPLE 3

4-acetoxy-9-amino-3,4-dihydroacridin-1(2H)-one

A solution of 9-amino-3,4-dihydroacridin-1(2H)-one N-oxide (5.4 g) and acetic anhydride (60 ml) was heated to reflux and then concentrated. The residue was stirred in saturated sodium bicarbonate solution for one hr. The mixture was filtered and the filter cake was washed with water and dried under vacuum at 40° C. for three hrs to yield 1.93 g of product, mp 208° C. (dec). An additional 1.38 g, mp 208° C. (dec), of product was obtained by extraction of the filtrate with ethyl acetate, evaporation of ethyl acetate extract, and trituration of the residue with diethyl ether; total 52% yield.

EXAMPLE 4

9-Amino-1,2,3,4-tetrahydro-1,4-acridinediol

To a solution of 3-acetoxy-9-amino-3,4-dihydroacridin-1(2H)-one (1.5 g) in dry tetrahydrofuran (75 ml), was added lithium aluminum hydride (1.0M in tetrahydrofuran, 11.1 ml) dropwise, with stirring. Stirring was continued for 15 mins. The reaction mixture was quenched with methanol, concentrated, and the residue was flash chromatographed (silica, 3:10:87 methanol:-triethylamine:dichloromethane). The appropriate fractions were collected and evaporated.

An additional experiment was run on the same scale. The fractions were combined and distributed between methyl ethyl ketone and 10% sodium hydroxide solution. The organic fraction was dried over anhydrous magnesium sulfate, filtered, and the filtrate was concentrated under vacuum. Recrystallization of the residue of the more polar fractions from water/methanol yielded 800 mg (31%) of 9-amino-1,2,3,4-tetrahydro-1,4-acridinediol, mp 200° C.(dec).

Analysis: Calculated for $C_{13}H_{14}N_2O_2$: 67.81% C; 6.13% H; 12.17% N. Found: 67.72% C; 6.28% H; 12.11% N.

Recrystallization of the residue of the less polar fractions from water gave 304 mg (11.9%) of 9-amino-1,2,3,4-tetrahydro-1,4-acridinediol, mp 183° C. (dec).

Analysis: Calculated for $C_{13}H_{14}N_2O_2$: 67.81%C; 6.13% H; 12.17% N. Found: 67.62% C; 6.33% H; 12.06% N.

EXAMPLE 5

N-[5-(Phenyldimethylsilyl)-3-oxocyclohex-1-enyl]-2-aminobenzonitrile

A solution of anthranilonitrile (3.33 g), and 5-(phenyldimethylsilyl)-1,3-cyclohexanedione (6.61 g), and toluene (180 ml) containing 0.51 g of p-toluenesulfonic acid monohydrate was heated under reflux with collection of water in a Dean-Stark trap. After 3 hr, the reaction mixture was diluted with ethyl acetate, and the solution was washed with saturated sodium bicarbonate solution and water, dried over anhydrous magnesium sulfate, filtered, and the filtrate was evaporated. The residue was flash chromatographed on silica gel, eluting with dichloromethane and then, successively 5%, 10%, and 15% ethyl acetate in dichloromethane. The appropriate fractions were collected and evaporated to give 6.37 g (68%) of product, mp 126°–129° C.

EXAMPLE 6

9-Amino-3,4-dihydro-3-(phenyldimethylsilyl)acridin-1(2H)-one

A mixture of N-[5-(phenyldimethylsilyl)-3-oxocyclohex-1-enyl]-2-aminobenzonitrile (6.3 g) in tetrahydrofuran (180 ml) containing potassium carbonate (2.76 g) and cuprous chloride (0.18 g) was refluxed for 4 hrs. The reaction mixture was diluted with methanol (100 ml) and then flushed over a column of Florisil. The appropriate fractions were collected and evaporated to give 5.05 g (80%) of product, mp 178°–180° C.

EXAMPLE 7

9-Amino-3,4-dihydro-3-(fluorodimethylsilyl)acridin-1(2H)-one

A mixture of 9-amino-3,4-dihydro-3-(phenyldimethylsilyl)acridin-1(2H)-one (5.0 g), dichloromethane (80 ml) and tetrafluoroboric acid etherate (25 ml) was stirred overnight at ambient temperature. The reaction mixture was poured into saturated potassium carbonate solution and extracted with ethyl acetate. The suspension was filtered through celite and the organic phase was separated. The aqueous phase was extracted with ethyl acetate and the combined organic phases were dried over anhydrous magnesium sulfate, filtered, and the filtrate evaporated to give 3.79 g (90%) of product, which is used in Example 8 without purification and without delay.

EXAMPLE 8

9-Amino-3,4-dihydro-3-hydroxyacridin-1(2H)-one

A solution 9-amino-3,4-dihydro-3-(fluorodimethylsilyl)acridin-1(2H)-one (3.7 g) 1:1-tetrahydrofuran:methanol (70 ml), potassium fluoride (7.45 g), and sodium bicarbonate (10.7 g) was chilled in an ice/water bath, and 30% aqueous hydrogen peroxide (44 ml) was added slowly. Upon completion of the addition, the bath was removed and stirring was continued for 3 hr. The reaction mixture was poured into water (250 ml) and a little diethyl ether was added. The mixture was filtered and the filter cake was washed with water and diethyl ether to give 2.6 g (89%) of product, mp 205° C. (dec).

EXAMPLE 9

9-Amino-1,2,3,4-tetrahydro-1,3-acridinediol maleate

A suspension of 9-amino-3,4-dihydro-3-hydroxyacridin-1(2H)-one (2.07 g) in tetrahydrofuran (125 ml), lithium triethylborohydride (1 molar in tetrahydrofuran, 27 ml) was allowed to stand for 0.5 hrs. The reaction mixture was quenched with methanol. The mixture was preadsorbed on silica, and flash chromatographed on silica gel (1:2:17-dichloromethane:triethylamine). The appropriate fractions were collected. Evaporation of the more polar fractions gave 0.541 (25.8%) of 9-amino-1,2,3,4-tetrahydro-1,3-acridinediol, mp 139°–141° C.

9-Amino-1,2,3,4-tetrahydro-1,3-acridinediol (mp 139°–141° C.) was dissolved in methanol and treated with maleic acid (1.1 eq.). Diethyl ether was added and the precipitate was collected to give the maleate, mp 158°–160° C.

Analysis: Calculated for $C_{13}H_{14}N_2O_2 \cdot C_4H_4O_4$: 58.96% C; 5.24% H; 8.09% N. Found: 58.72% C; 5.27% H; 7.99% N.

Evaporation of the less polar fractions gave 0.784 g (37.3%) of 9-amino-1,2,3,4-tetrahydro-1,3-acridinediol, mp 158°–162° C. The maleate had mp 179°–180° C.

Analysis: Calculated for $C_{13}H_{14}N_2O_2 \cdot C_4H_4O_4$: 58.96% C; 5.24% H; 8.09% N. Found: 58.95% C; 5.28% H; 8.15% N.

REACTION SCHEME A

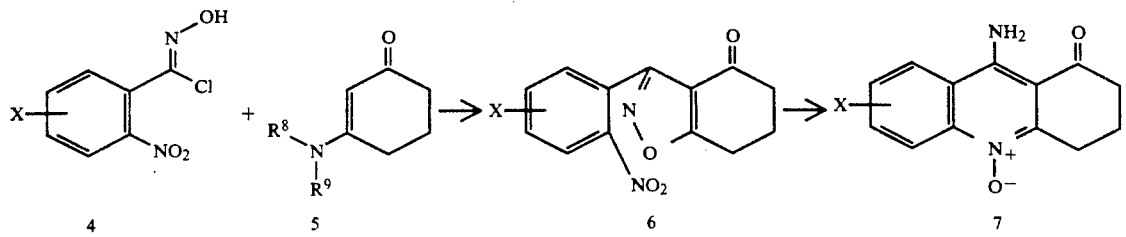

REACTION SCHEME A -continued

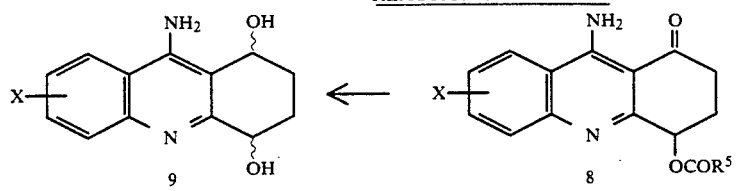

wherein $R^5$, $R^8$, $R^9$, and X are as hereinbeforedefined.

REACTION SCHEME B

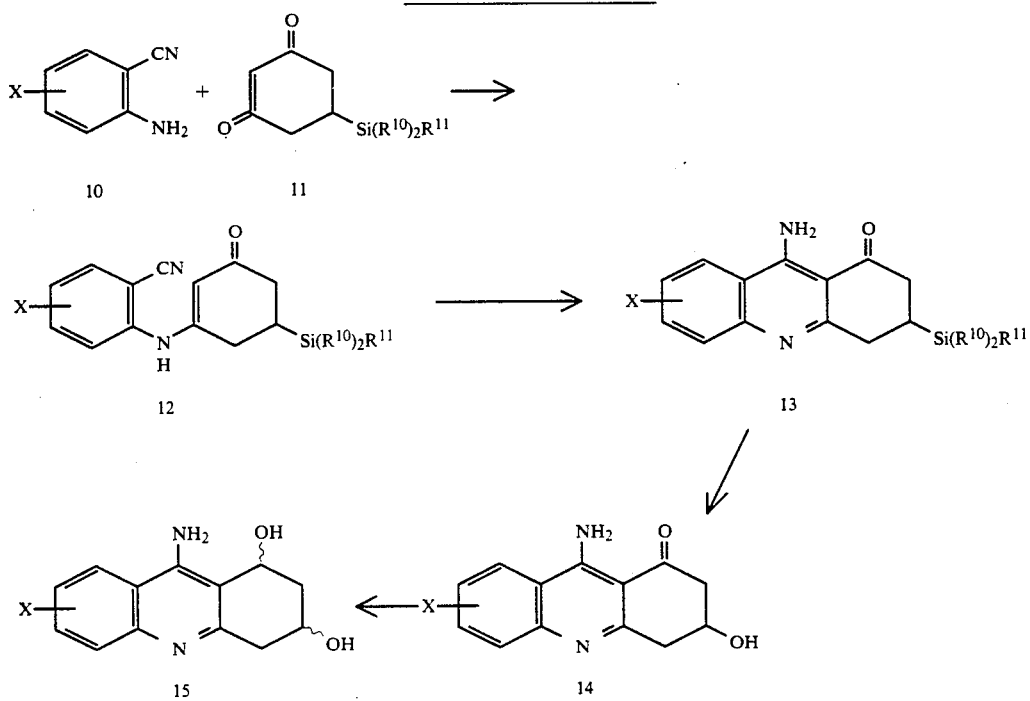

wherein $R^{10}$, $R^{11}$, and X are as hereinbeforedefined.

We claim:

1. A compound of the formula

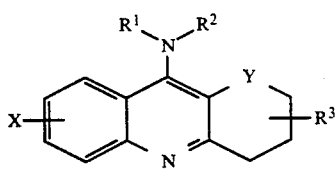

wherein Y is C=O; $R^1$ is hydrogen or loweralkyl; $R^2$ is hydrogen, loweralkyl, or phenylloweralkyl; $R^3$ is $OR^4$ wherein $R^4$ is hydrogen, $COR^5$ wherein $R^5$ is loweralkyl, X is hydrogen, loweralkyl, halogen, loweralkoxy, hydroxy, or trifluoromethyl, the geometric or optical isomers thereof, N-oxides thereof, or the pharmaceutically acceptable acid addition salts thereof.

2. A compound according to claim 1 wherein Y is C=O and $R^3$ is $OR^4$ wherein $R^4$ is hydrogen.

3. The compound according to claim 2 which is 3-acetoxy-9-amino-3,4-dihydroacridin-1(2H)-one.

4. The compound according to claim 3 which is 9-amino-1,2,3,4-tetrahydro-1,4-acridinediol, having a melting point of 200° C. (dec).

5. The compound which is 9-amino-3,4-dihydroacridin-2(2H)-one N-oxide.

6. A method of relieving memory dysfunction in mammals comprising administering to a mammal requiring memory dysfunction relief, a memory dysfunction relieving effective amount of a compound of claim 1.

7. A memory of dysfunction relieving composition comprising and adjuvant and as the active ingredient, a memory dysfunction relieving effective amount of a compound of claim 1.

* * * * *